United States Patent [19]

Ricci

[11] 4,299,573
[45] Nov. 10, 1981

[54] MANUFACTURE OF DENTURES
[75] Inventor: Mario Ricci, Fossano, Italy
[73] Assignee: Major Prodotti Dentari S.p.A., Mocalieri, Italy
[21] Appl. No.: 125,320
[22] Filed: Feb. 28, 1980
[51] Int. Cl.³ .............................................. A61C 13/00
[52] U.S. Cl. .................................... 433/167; 433/141
[58] Field of Search .................... 433/71, 68, 40, 37, 433/141, 167

[56] References Cited
U.S. PATENT DOCUMENTS
2,183,624 12/1939 Schwartz ............................. 433/71
2,313,535 3/1943 Glitzke ................................. 433/71

Primary Examiner—Robert Peshock
Attorney, Agent, or Firm—Sughrue, Mion, Zinn, Macpeak and Seas

[57] ABSTRACT

A device for facilitating the positioning and mounting of rear teeth on dentures, comprises a small, elongate plate which bears on respective faces the impressions of the occlusal parts of the upper and lower rear teeth respectively, and is provided on one side with a pair of parallel cantilever arms. The impressions are provided with holes in correspondence with the cusps of the upper and lower teeth to ensure the correct positioning of the teeth on the respective dentures, while the arms locate the plate correctly relative to a predetermined occlusal plane of the teeth.

7 Claims, 6 Drawing Figures

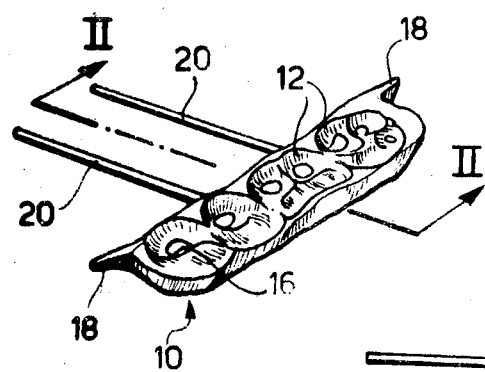
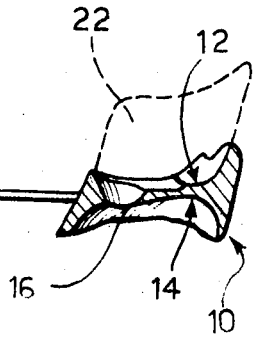
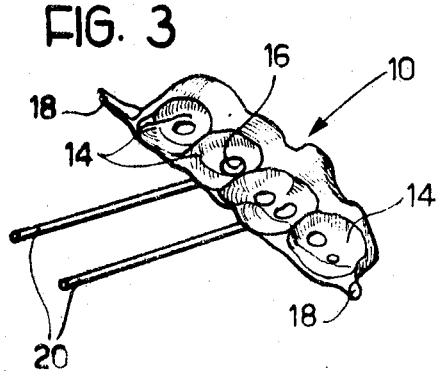
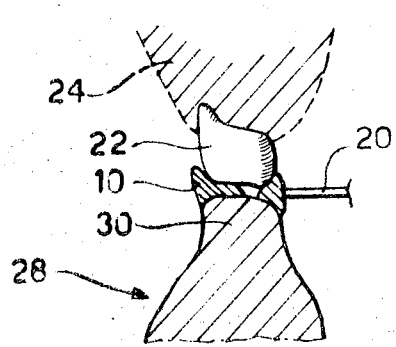
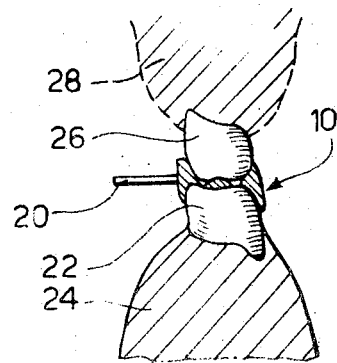

MANUFACTURE OF DENTURES

The present invention relates to the manufacture of dentures, and is concerned, more particularly with the positioning and mounting of rear teeth on both full and partial dentures.

The operation of positioning and mounting rear teeth on dentures, particularly when there are to be cooperating upper and lower dentures, is laborious and time-consuming, since it is difficult to match accurately the occlusal parts of the upper and lower teeth, that is, the parts of the teeth which come together when the jaws are shut, to ensure a comfortable fit of the finished dentures.

The object of the present invention is to provide a device for facilitating the positioning and mounting of rear teeth on dentures.

Accordingly, the present invention provides a device for facilitating the positioning and mounting of rear teeth on dentures, characterised in that the device comprises an elongate plate bearing on respective faces impressions of the occlusal parts of upper and lower rear teeth respectively, the impressions serving to position the teeth correctly during mounting on the respective dentures, and being provided with holes in correspondence with the cusps of at least the upper teeth.

One embodiment of the invention will now be more particularly described, by way of example with reference to the accompanying drawings, in which:

FIG. 1 is a perspective view from above of a device according to the invention, for facilitating the positioning and mounting of rear teeth on dentures; FIG. 2 is a section taken along the line II—II of FIG. 1;

FIG. 3 is a perspective view of the device of FIG. 1 from below;

FIG. 5 is a section taken along the line V—V of FIG. 4;

FIG. 7 is a section taken along the line VII—VII of FIG. 6.

Figure 4:
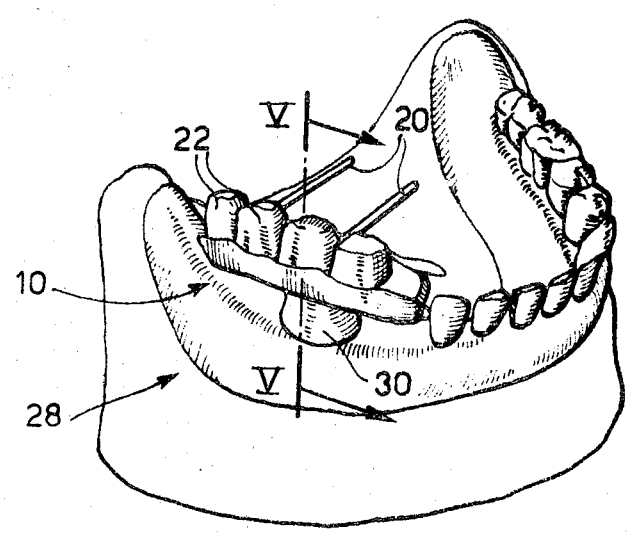
FIG. 4 shows the device of FIG. 1 in use for mounting rear teeth on an upper denture.

Referring now to the drawings, there is shown a device for facilitating the positioning and mounting of rear teeth on dentures, comprising a small elongate plate 10 of cast metal or plastics. The plate 10 is formed with an axially extending lug 18 at each end, adjacent one side, and is provided, on this side, with a pair of laterally projecting parallel cantilever arms 20 which extend substantially in the plane of the plate 10.

Figure 6:
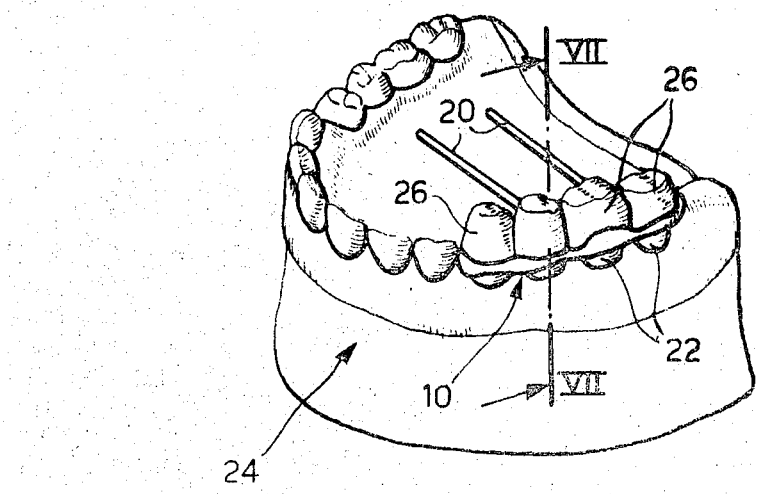
FIG. 6 shows the device of FIG. 1 in use for mounting rear teeth on a lower denture.

One face of the plate 10 bears four impressions 12, each corresponding to the occlusal part of a respective rear upper tooth 22 which is to be mounted on an upper denture 24 (FIG. 6). Similarly, the other face of the plate 10 bears four impressions 14 corresponding to the occusal parts of the rear lower teeth 26 to be mounted on a lower denture 28 (FIG. 4). The impressions 12,14 on each face of the plate 10 are interconnected by holes 16 located in correspondence with the cusps of the teeth 22, 26.

When the teeth 22,26 are to be mounted on the dentures 24,28, the latter are secured to an articulated holder of known type (not shown) which is positioned so that the dentures 24,28 are arranged in their normal positions of use. As shown in FIG. 4, a support element 30 of wax or resin is applied temporarily to the part of the lower denture 28 on which the teeth 26 will be mounted and, as can be better seen in FIG. 5, the top of the support element 30, approximating to the height of the teeth 26 to be mounted, extends into a predetermined plane of occlusion for the teeth 22,26 of the upper and lower dentures 24,28.

The plate 10 is placed on the support element 30, being arranged with the impressions 12 of the upper teeth 22 uppermost and the cantilever arms 20 extending towards the middle of the denture 28, and a respective upper tooth 22 then inserted into each impression 12. By controlling the position of the general plane in which the arms 20 lie, it is possible to adjust the position of the plate 10 until if coincides exactly with the predetermined plane of occlusion. This operation is facilitated when the teeth 22,26 are to be mounted on both sides of the denture 28, since the cantilever arms 20 of both plates can be located in the same plane to better define the predetermined plane of occulusion. The correct position of the rear of the plate 10 is given when one of lugs 18 comes into contact with the inner, lingual, side of the retromolar area of the denture 28.

After the plate 10 has been positioned exactly, the articulated holder is closed so that the bases of rear upper teeth 22 are then correctly positioned on the upper denture 24, and fixed thereto by a previously applied layer of wax or resin. The articulated holder is then reopened and inverted to bring the upper denture 24, and therefore, the plate 10, into the position as shown in FIG. 6, where other face of plate 10 and the impressions 14 of the lower teeth 26 are uppermost. The lower teeth 26 are then inserted into the respective impressions 14.

The plate 10 is now in the correction position relative to the plane of occlusion, since its said one face now rests on the occlusal surfaces of the upper teeth 22. At this stage, the correction position of the rear of the plate 10 is again given by one of the lugs 18 coming into contact with the inner, lingual, side of the retromolar area of the denture 24. The bases of the rear lower teeth 26 are correctly positioned on the lower denture 28 upon closing the holder, and are fixed by a layer of wax or resin previously substituted for the support element 30.

When teeth 22, 26 are mounted on the dentures 24, 28, the holes 16 through the plate 10, made in correspondence with the cusps of the teeth, ensure that upper and lower teeth 22, 26 come together correctly in the occluded position, that is, when the wearer's jaws are shut.

What is claimed is:

1. A device for facilitating the positioning and mounting of rear teeth on dentures, comprising an elongate plate, respective faces of said plate defining impressions of occlusal parts of upper and lower said teeth respectively, said faces further having, within said impressions, holes corresponding to the positions of cusps of at least said upper teeth, whereby said impressions position said teeth correctly during mounting on respective said dentures.

2. A device as defined in claim 1, wherein said plate is provided on one side with a pair of parallel laterally projecting positioning arms which, during mounting, serve to position said plate correctly relative to a predetermined plane of occlusion of said teeth.

3. A device as defined in claim 1 or claim 2, wherein each end of said plate is provided with a respective axially extending lug which, during mounting, abuts an inner, lingual, side of the retromolar area of the denture to position correctly the rear of said plate.

4. A method for positioning and mounting rear teeth on dentures, comprising the steps of:
  (a) providing an upper denture support and a lower denture support;
  (b) mounting the upper and lower denture supports on an articulated holder;
  (c) providing at least one elongate plate, respective surfaces of said plate having depressions of a form corresponding to the occlusal parts of upper and lower teeth which are to be mounted on said upper and lower denture supports;
  (d) mounting a support element on the part of the lower denture support on which the lower rear teeth are to be mounted, said support element having a top surface substantially extending in a predetermined plane of occlusion of the rear teeth which are to be mounted;
  (e) placing said elongate plate onto said top surface of the support element and positioning such plate in said predetermined plane of occlusion;
  (f) positioning the upper rear teeth, which are to be mounted onto said upper denture support, on the depressions of the upwardly facing surface of said plate, with the occlusal parts of said teeth resing on said depressions;
  (g) applying a layer of fixing material onto the part of the upper denture support on which the upper rear teeth are to be mounted;
  (h) closing the articulated holder bringing said part of the upper denture support which is covered by fixing material into engagement with said upper rear teeth, thereby fixing the latter to said upper denture support;
  (i) opening the articulated holder and inverting the same so as to bring the lower denture support in uppermost position;
  (j) removing the support element from the lower denture support;
  (k) placing said plate in a position resting on the occlusal parts of the upper teeth fixed to the upper denture support;
  (l) positioning the lower rear teeth which are to be mounted onto said lower denture support on the depressions of the upwardly facing surface of said plate, with the occlusal parts of said teeth resting on said depressions;
  (m) applying a layer of fixing material on the part of the lower denture support on which the lower rear teeth are to be mounted;
  (n) closing the articulated holder, bringing said part of the lower denture support which is covered by fixing material into engagement with said lower rear teeth, thereby fixing the latter to said lower denture support.

5. A method as set forth in claim 4, wherein said plate is provided on one side with a pair of parallel laterally projecting positioning arms, which, during mounting of the plate on said support element, serve to position said plate correctly in said predetermined plane of occlusion.

6. A method as set forth in claim 2, wherein each end of said plate is provided with a respective axially extending lug which, during mounting of said plate on said support element, serve to position said plate correctly in said predetermined plane of occlusion.

7. A method as set forth in claim 4, wherein said plate is provided with holes within said depressions which ensure that upper and lower rear teeth come together correctly in the occluded position.

* * * * *

UNITED STATES PATENT AND TRADEMARK OFFICE
CERTIFICATE OF CORRECTION

PATENT NO. : 4,299,573
DATED : November 10, 1981
INVENTOR(S) : Mario RICCI

It is certified that error appears in the above—identified patent and that said Letters Patent is hereby corrected as shown below:

Please add the Foreign Application Priority Data as follows:

--March 6, 1979........Italy............53039-B/79--

Please change the spelling of the Assignee's Address as follows:

Delete "Mocalieri" and insert therefor --Moncalieri--.

Signed and Sealed this

Eighth Day of June 1982

[SEAL]

Attest:

Attesting Officer

GERALD J. MOSSINGHOFF

Commissioner of Patents and Trademarks